(12) United States Patent
Kanazawa et al.

(10) Patent No.: US 9,414,744 B2
(45) Date of Patent: Aug. 16, 2016

(54) OPTOMETRY APPARATUS

(71) Applicant: NIDEK CO., LTD., Aichi (JP)

(72) Inventors: Yuichiro Kanazawa, Aichi (JP); Noritsugu Nozawa, Aichi (JP); Ryoji Suzuki, Aichi (JP); Yukito Hirayama, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/136,480

(22) Filed: Dec. 20, 2013

(65) Prior Publication Data

US 2014/0185012 A1 Jul. 3, 2014

(30) Foreign Application Priority Data

Dec. 28, 2012 (JP) ................................ 2012-286484

(51) Int. Cl.
*A61B 3/10* (2006.01)
*A61B 3/02* (2006.01)
*A61B 3/032* (2006.01)
*A61B 3/18* (2006.01)

(52) U.S. Cl.
CPC .. *A61B 3/032* (2013.01); *A61B 3/18* (2013.01)

(58) Field of Classification Search
CPC ........... A61B 3/032; A61B 3/18; A61B 3/103
USPC ........................... 351/205, 209, 237, 239, 240
See application file for complete search history.

(56) References Cited

U.S. PATENT DOCUMENTS

| | | | |
|---|---|---|---|
| 4,403,842 | A | 9/1983 | Aulhorn et al. |
| 2002/0047997 | A1 | 4/2002 | Hayashi et al. |
| 2004/0218143 | A1 | 11/2004 | Terabe |
| 2009/0244486 | A1 | 10/2009 | Oda |
| 2012/0133890 | A1 | 5/2012 | Rathjen |
| 2013/0069973 | A1 | 3/2013 | Ichikawa |

FOREIGN PATENT DOCUMENTS

| | | | |
|---|---|---|---|
| EP | 1472969 | | 11/2004 |
| JP | 06054805 | A * | 3/1994 |
| JP | 06-197867 | | 7/1994 |
| JP | 2006014766 | A2 | 1/2006 |
| JP | 2009-207571 | | 9/2009 |
| JP | 2011072432 | A2 | 4/2011 |
| JP | 2011218076 | A2 | 11/2011 |

OTHER PUBLICATIONS

Extended European Search Report dated Aug. 14, 2014 issued in the corresponding European patent application No. 13199713.2.
Partial European Search Report dated Mar. 28, 2014 filed in the corresponding European patent application No. 13199713.2.

* cited by examiner

*Primary Examiner* — Mahidere Sahle
(74) *Attorney, Agent, or Firm* — Rankin, Hill & Clark LLP

(57) ABSTRACT

An optometry apparatus includes: a housing accommodating a concave mirror disposed on a reference axis; and a display disposed outside the housing and out of the reference axis for projecting a target light flux onto the concave mirror. The concave mirror is configured to reflect the target light flux output from the display toward an examinee's eye along the reference axis.

18 Claims, 9 Drawing Sheets

FRONT VIEW    PLAN VIEW

FRONT VIEW    PLAN VIEW

OPTOMETRY APPARATUS

CROSS-REFERENCE TO RELATED APPLICATION

This application is based on Japanese Patent Application No. 2012-286484 filed with the Japan Patent Office on Dec. 28, 2012, the entire content of which is hereby incorporated by reference.

BACKGROUND

1. Technical Field

The present disclosure relates to an optometry apparatus that presents an examination target for visual function inspection.

2. Related Art

A known optometry apparatus includes a target plate, a light source such as a halogen lamp for illuminating the target plate, a beam splitter disposed at an angle, and a concave mirror (see JP-A-06-197867, for example). In this optometry apparatus, a target light flux from the target plate illuminated by the light source is guided via the beam splitter and the concave mirror to the examinee's eye. Thus, the examination target is presented to the examinee's eye. The apparatus includes a protection cover on the front face of the housing. The protection cover has a presentation window with a transparent plate. The target light flux is output toward the examinee's eye through the transparent plate of the presentation window.

SUMMARY

1. An optometry apparatus includes: as housing accommodating a concave mirror disposed on a reference axis; and a display disposed outside the housing, and out of the reference axis for projecting a target light flux onto the concave mirror. The concave mirror is configured to reflect the target light flux output from the display toward an examinee's eye along the reference axis.

DETAILED DESCRIPTION

Figure 1:
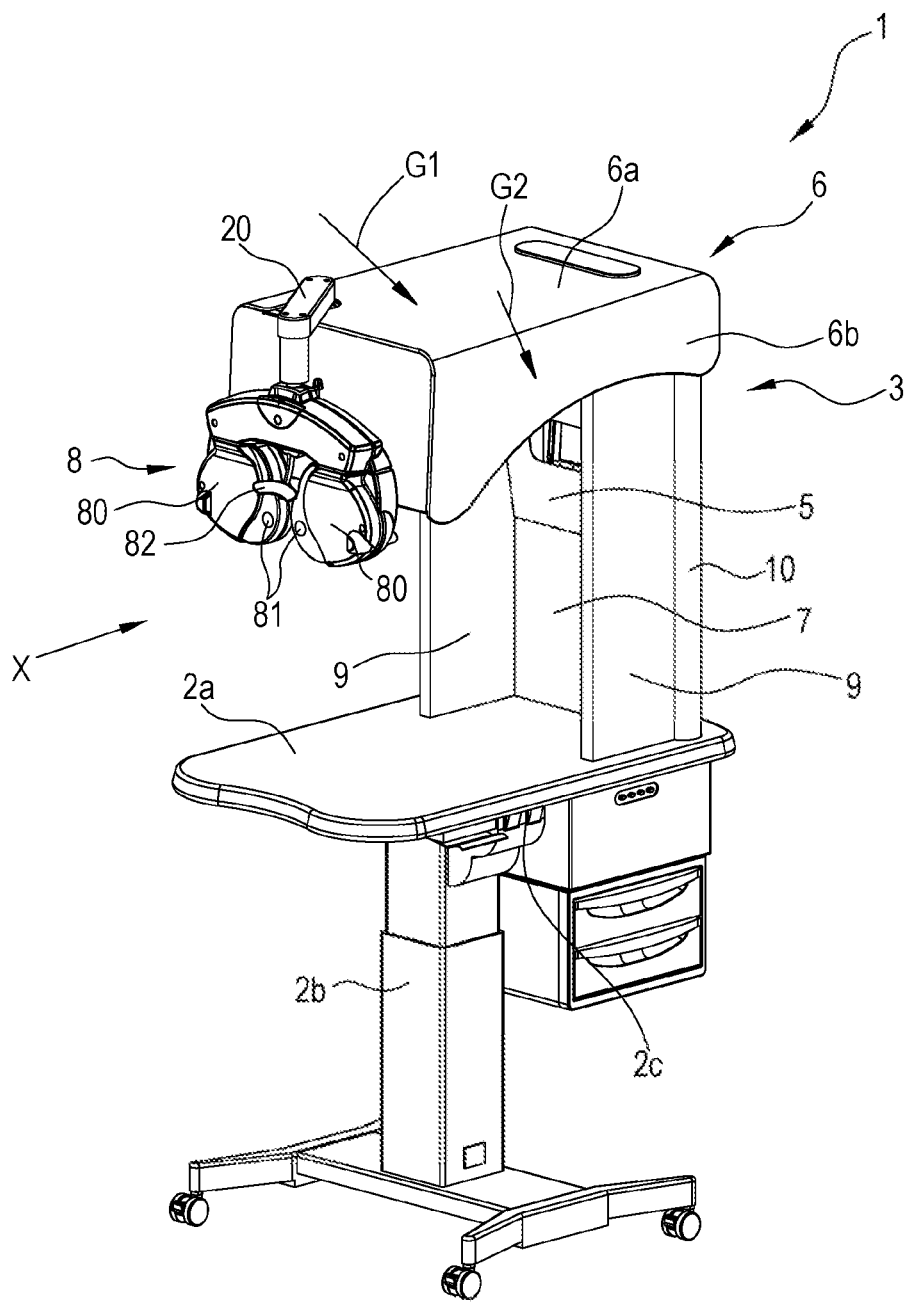
FIG. 1 is an exterior view an optometry apparatus according, to an embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the apparatus described in JP-A-06-197867, strong light from outside the housing may be reflected by the transparent plate in the presentation window, and the reflected light may enter the examinee's eye. In this case, the accuracy of visual function examination may be decreased.

An object of the present disclosure is to provide an optometry apparatus that can perform target presentation for accurate examination.

An optometry apparatus according to an embodiment in the present disclosure (the present apparatus) includes the following configuration.

(1) The optometry apparatus includes: the housing having as presentation window for presenting an examination target, in a frame to the examinee's eye at a distance of at least 20 cm; an upper shield member for blocking disturbance light entering the presentation window from above the examinee's eye; and a lower shield member for shielding an area under the presentation window.

(2) In the present apparatus, the upper shield member and the lower shield member may have the same color at least in the range of a predetermined visual field angle of the examinee's eye at an optometry position.

(3) The present apparatus may further include a lateral shield member extending from each of left and right sides of the presentation window toward the examinee, and optically shielding a space extending from the presentation window toward the examinee with a predetermined distance. The lateral shield member may have the same color as the upper shield member and the lower shield member at least in the range of the predetermined visual field angle of the examinee's eye at the optometry position.

(4) The present apparatus may have a configuration where the lower shield member extends from under the presentation window toward the examinee, and is configured to optically shield a space extending from the presentation window toward the examinee with a predetermined distance.

(5) The present apparatus may further include a target projection portion configured to protect a target light flux onto the housing. The housing may further include a concave mirror. The target projection portion may be configured to project the target light flux onto the examinee's eye via the concave mirror. The upper shield member may be configured to shield an optical path of the target light flux from above.

According to the present apparatus, target presentation for accurate examination can be performed. Further, the influence of disturbance light can be decreased.

In the following, an optometry apparatus according to an embodiment of the present disclosure will be described with reference to the drawings. FIGS. 1 to 12 are diagrams explaining configurations of the optometry apparatus according to the present embodiment.

Outline of Apparatus

The outline of an optometry apparatus 1 according to the embodiment of the present disclosure will be described. The optometry apparatus 1 (see FIG. 1) is provided with a target presentation unit 3 and a subjective eye refractive power measurement unit 8 (hereafter simply referred to as the "measurement unit"). The optometry apparatus 1 implements an examination (distance-examination) for distance-visual function of the examinee's eye (far-vision visual function), and an examination (near-examination) for near-visual function (near-vision visual function). In the optometry apparatus 1, the target presentation unit 3 presents a target to the examinee's eye via a distance-examination optical path. The measurement unit includes as pair of left and right lens chamber units 80. The lens chamber units 80 include examination windows 81, and optical elements (such as corrective lenses) disposed in the examination windows 81 in a switchable manner. The arrangement (position) of the optical elements can be switched. For example, in the optometry apparatus 1, the examinee's eye peeks through the examination windows 81 of the measurement unit 8. The examinee's eye is then presented with the examination target, and the distance-visual function of the examinee's eye is examined.

The optometry apparatus 1 also includes an optometry table (optometry table unit) 2 and a holding portion (holding unit) 10. The holding unit 10 holds the target presentation unit 3. The holding unit 10 also holds the measurement unit 8 such that the examination windows 81 are positioned at the same height as a reference axis L1. For example, the holding unit 10 holds the target presentation unit 3 above the optometry table unit 2.

The target presentation unit 3 may not be configured to be held on the optometry table unit 2 by the holding unit 10. The holding unit 10 may be of a wall-hanging type. In this case, the target presentation unit 3 is installed on the wall.

The target presentation unit 3 includes a concave mirror 50 (see FIG. 3), and a target projection portion (such as a display 45). The target projection portion (display 45) projects a target light flux onto the concave mirror 50. In the target presentation unit 3, the target light flux, output from the display 45 is reflected by the concave mirror 50. Thus, the target presentation unit 3 presents the target at an optically predetermined distance-examination distance (distance from the examinee's eye). Namely, the concave mirror 50 is disposed at an optically predetermined examination position for distance-examination (position with respect to the examinee's eye) on the reference axis L1. In this way, the target light flux is projected on the examinee's eye through the concave mirror 50.

For example, in the target presentation unit 3, the concave mirror 50 and the display 45 are disposed such that a direction normal to the screen of the display 45 is inclined with respect to an optical as O1 the concave mirror 50. In this case, the optical path of the target light flux is displaced from the optical axis O1 of the concave mirror 50.

As the display 45, a liquid crystal display (LCD) or an organic electro luminescence (EL) display may be used.

The concave mirror 50 is disposed on a reference axis (central axis of the left and right eyes) L1 along the direction of the visual line of the examinees eye viewing the front (frontal direction), for example. The concave mirror 50 may be housed in a housing 5.

For example, the housing, 5 is disposed in the frontal direction of the measurement unit 8 (see FIG. 1). The housing 5 includes a presentation window (such as a transparent panel 52). The transparent panel 52 is disposed in front of the concave mirror 50 on the reference axis L1. The transparent panel 52 transmits the target light flux from the display 45. The transparent panel 52 also re-transmits the target light flux reflected by the concave mirror 50 so that the target light flux can exit the housing 5. The optometry apparatus 1 (target presentation unit 3) presents the examination target to the examinees eye at a distance of at least 20 cm from the presentation window (transparent panel 52).

The target presentation unit 3 is configured to present the target without going through a beam splitter that would produce a large loss in the amount of light of the target light flux. Thus, in the target presentation unit 3, luminance required for examination, such as visual acuity examination, can be ensured without using a display that emits large amount of light. Accordingly, the examination can be performed accurately. Further, the housing, 5 does not include the beam splitter, so that the housing 5 can be made thin. Thus, the optometry apparatus 1 can provide a space-saving optometry apparatus.

In the following, various members will be described in concrete terms, in the order of the display 45 (see FIG. 3), the transparent panel 52, the optical path switching unit 60, and the subjective eye refractive power measurement unit. The members may be combined as needed, or implemented as independent members.

Display

The display 45 is disposed outside the housing 5 and out of the reference axis L1, The display 45 is disposed outside the range of a predetermined visual field angle of the examinee's eye peeking through the examination windows 81 of the measurement unit 8.

For example, the display 45 is disposed outside the housing 5 at a position such that the target light flux from the display 45 travels from outside the housing 5 toward the concave mirror 50 via the transparent panel 52. For example, the display 45 is disposed in the vicinity of the measurement unit 8, and outputs the target light flux toward the concave mirror 50 from the examinee's eye side. For example, the display 45 is disposed in the vicinity of a forehead rest 82 of the measurement unit 8. For example, the display 45 is disposed above the forehead rest 82 of the measurement unit 8 (see FIG. 1).

The display 45 (see FIG. 3) is disposed as described above, whereby the visual field, of the examinee can be made wider. When the examinee observes a flit optotype inside the housing 5 through the transparent panel 52, the examinee does not see the display 45, is a superfluous structure located closer to the examinee than a protection panel 51. Thus, the examinee is suppressed or prevented from gazing the display 45. As a result, the occurrence of accommodation by the examinee's eye due to the examinee seeing a structure other than the target during the distance-examination can be decreased, whereby the visual function examination can be performed accurately.

The display 45 may not be disposed outside the range of the predetermined visual field angle when the examinee (examinee's eye) is peeking through the examination windows 81 of the measurement unit 8. For example, the display 45 is disposed near the forehead of the examinee outside the housing 5 and at a position such that the target light flux from the display 45 travels from outside the housing 5 through the transparent panel 52 toward the concave mirror 50. Thus, the display 45 may be disposed near the forehead of the examinee. Accordingly, when the target light flux is output toward the concave mirror 50, the angle of incidence of the target light flux on the concave mirror 50, and the angle of reflection of the target light flux from the concave mirror 50 are decreased, whereby target distortion can be decreased.

Transparent Panel

The housing 5 is fitted with the transparent panel 52. The transparent panel 52 is disposed at an angle such that the direction normal to the front face thereof (facing the examinee's eye) is inclined with respect to the reference axis L1. The inclination angle of the transparent panel 52 is set such that the reflected light produced by the output light from the display 45 being reflected by the front face of the transparent panel 52 travels in a direction away from the examinee's eye at the predetermined position.

Thus, the strong light from the display 45 can be restricted from being reflected by the transparent panel 52 and then entering the examinee's eye, which would interfere with the examinee's observation of the target. Further, disturbance light from the background rearwardly of the examinee, and disturbance light from above the optometry apparatus 1 can be restricted from being reflected by the transparent panel 52 and then entering the examinee's eye, which would interfere with the examinee's observation of the target.

The housing 5 may further include a shield member (shield portion 53) disposed on the front face side of the concave mirror 50 and around the transparent panel 52. In this case, the transparent panel 52 surrounded by the shield portion 53 may include the presentation window for the observation of the target inside the housing 5 by the examinee's eye. The shield portion 53 makes it difficult to see the internal structure of the housing 5. Of course, the presentation window may be formed only by the transparent panel 52 and may not include the shield portion 53.

The optometry apparatus 1 may be further provided with an upper shield member (shield cover 6). The upper shield member covers the top of the optical path between the transparent panel 52 and the display 45, for example. The optometry apparatus 1 may be further provided with a lateral shield member (shield cover 6). The lateral shield member laterally covers the optical path between the transparent panel 52 and the display 45, for example. By providing these shield members, the entry of disturbance light from a fluorescent light and the like into the optical members within the apparatus can be suppressed.

The shield cover 6 according to the present embodiment includes the upper shield member and the lateral shield member. However, the upper shield member and the lateral shield member may be separate members. The optometry apparatus 1 may include at least one of the upper shield member and the lateral shield member.

Optical Path Switch Portion

The optometry apparatus 1 is provided with an optical path switch portion and an angle changing portion (first angle changing portion). The optical path switch portion switches the optical path between a distance-examination optical path and a near-examination optical path (near-vision examination optical path). The near-examination optical path is an optical path for guiding the target light flux from the display 45 to the examinee's eye without going through the concave mirror 50. The angle changing portion (first angle changing portion) changes the inclination angle of the screen of the display 45 between distance-examination and near-examination.

The optical path switch portion switches the optical path between the distance-examination optical path and the near-examination optical path. At the time of the switching, the angle changing portion changes the inclination angle of the screen of the display 45 such that the examinee (examinee's eye) can observe the screen of the display 45 positioned vertically with respect to the reference axis L1.

The optical path switch portion may include a reflective member (reflective mirror) 62 that can be inserted in or removed from the interval between the examinee's eye and the concave mirror 50. The reflective member (reflective mirror) 62 is disposed at an optically predetermined examination position for near-examination (position with respect to the examinee's eye) on the reference axis L1 between the concave mirror 50 and the examinee's eye. The reflective mirror 62 is configured to reflect the target light flux output from the display 45 toward the examinee's eye along the reference axis L1.

The optical path switch portion (optical path switching unit 60) switches the optical path between the distance-examination optical path and the near-examination optical path by inserting the reflective member 62 in or removing it from between the examinee's eye and the concave mirror 50. Examples of the reflective member 62 include a planar mirror, a convex mirror, and a concave mirror. In this case, the angle changing portion, when switching to the near-examination optical path, for example, changes the inclination angle of the screen of the display 45 such that the direction normal to the screen of the display 45 is substantially aligned with the direction of the light (virtual light) travelling along the reference axis L1 from the examinee's eye and reflected by the reflective member 62.

The angle changing portion, when switching to the distance-examination optical path, changes the inclination angle of the screen of the display 45 such that the direction normal to the screen of the display 45 is substantially aligned with the direction of the light (virtual light) travelling from the examinee's eye along the reference axis L1 and reflected by the concave mirror 50. Namely, when switching to the distance-examination optical path, the angle changing portion changes the inclination angle of the screen of the display 45 such that the target light flux output in the direction normal to the screen of the display 45 is reflected by the concave mirror 50 in the direction of the reference axis L1 toward the examinee's eye.

As described above, the optical path switch portion, in order to switch the optical path, inserts the reflective member for reflecting the target light flux from the display 45 and guiding the target light flux to the examinee's eye into, or removes it out of the optical path between the examinee's eye and the concave mirror 50. Alternatively, the optical path switch portion may be provided with a moving portion for moving the display 45 in the optical path between the examinee's eye and the concave mirror 50 in order to switch the optical path. In this way, the optical path can be easily switched between the optical path for distance-examination and the optical path for near-examination. When the optical path is switched, the inclination angle of the display 45 is changed. Thus, the target with decreased distortion can be projected onto the examinee's eye before and after the optical path switching. Accordingly, target presentation for accurate examination can be performed by the display 45 displaying the target.

According to a modification, the optical path switch portion (optical path switching unit 60) may be provided with a reflective member inclination angle changing portion (second angle changing portion) for changing the inclination angle of the reflective member. In this case, the optical path switch portion (optical path switching unit 60) moves the reflective member 62 inserted between the examinee's eye and the concave mirror 50 on the reference axis L1. At the same time, the reflective member inclination angle changing portion changes the inclination angle of the reflective member 62 such that the target light flux output from the display 45 can be reflected by the reflective member 62 toward the examinee's eye along the reference axis L1. As a result, the near-examination distance of the near-examination optical path is changed. The angle changing portion also changes the inclination angle of the screen of the display 45 such that as described above, the direction normal to the screen of the display 45 is substantially aligned with the direction of the light travelling from the examinees eye along the reference axis L1 and reflected by the reflective member 62. Thus, not just the distance-examination and the near-examination but also an examination for an intermediate distance can be performed.

Subjective Eye Refractive Power Measurement Unit

The measurement unit 8 is moved between an examination position in front of the examinee's eyes and a withdrawn position depending on whether the measurement unit 8 is used for visual function examination.

For example, the holding unit 10 is provided with a support portion (such as a support arm 20). The support portion movably supports the measurement unit 8 between the examination position in front of the examinee's eyes and the withdrawn position.

The holding unit 10 includes a first holding member (support column) 10*a* and a second holding member (upper support column) 10*b* extending from the support column 10*a*, for example. The support column 10*a* holds the housing at a predetermined distance from the measurement unit 8 placed at the examination position. The upper support column 10*b* extends from the support column 10*a*. The upper support column 10*b* extends from the top of the housing 5 toward the examinee so as to hold the display 45. The support portion is connected to the upper support column 10*b*. Namely, the support portion is disposed on the target presentation unit 3 via the holding unit 10.

The support portion may include the support arm 20 and/or a support member (such as a support column).

The support arm 20 as the support portion is connected to the upper support column 10*b* and configured to be rotated about a connected position O (see FIGS. 7A and 7B), for example. The support arm 20 can move the measurement unit 8 between the examination position and the withdrawn position by being rotated. In this way, the size of the optometry apparatus 1, i.e., the space required by the apparatus, can be decreased.

According to the present embodiment, preferably, the connected position O may be located at a position displaced from the central axis C of the optometry apparatus 1 in an up-down direction of the sheet of the drawing (plan views of FIGS. 7A and 7B) (in a direction substantially horizontal with respect to the upper face of the shield cover (exterior cover) 6. When the connected position O is displaced from the central axis C of the optometry apparatus 1, the measurement unit 8 can be moved by rotating the support arm 20 in a small range of movement. Thus, when the measurement unit 8 is moved, the range of movement of the support arm 20 can be decreased. Accordingly, the chances of the support arm 20 or the measurement unit 8 coming into contact with the examiner can be decreased.

For example, the support member as the support portion is provided with an up-down moving portion such as a known telescopic pipe mechanism) and attached to the upper support column 10*b*. The up-down moving portion is configured to move the measurement unit 8 between the examination position and the withdrawn position above the examination position. Thus, the measurement unit 8 can be moved between the examination position and the withdrawn position. In this way, when the measurement unit 8 is moved, the measurement unit 8 does not traverse the examiner's face. Accordingly, the chances of the measurement unit 8 coming into contact with the examiner can be decreased.

According to the present embodiment, the support portion is connected to the measurement unit 8. Further, the support portion is disposed on the target presentation unit 3 via the holding unit 10. However, the support portion may be connected to the target presentation portion (target presentation unit 3) without the intermediary of the holding unit 10.

Embodiment

Figure 2:
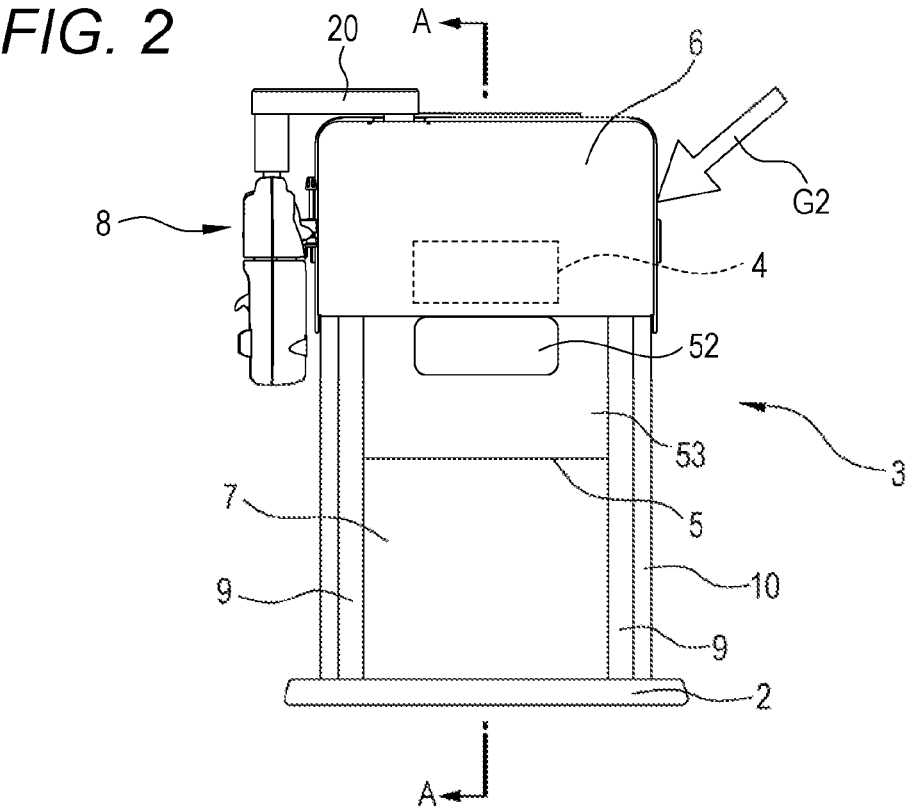
FIG. 2 is a frontal vive of the optometry apparatus.
Figure 3:
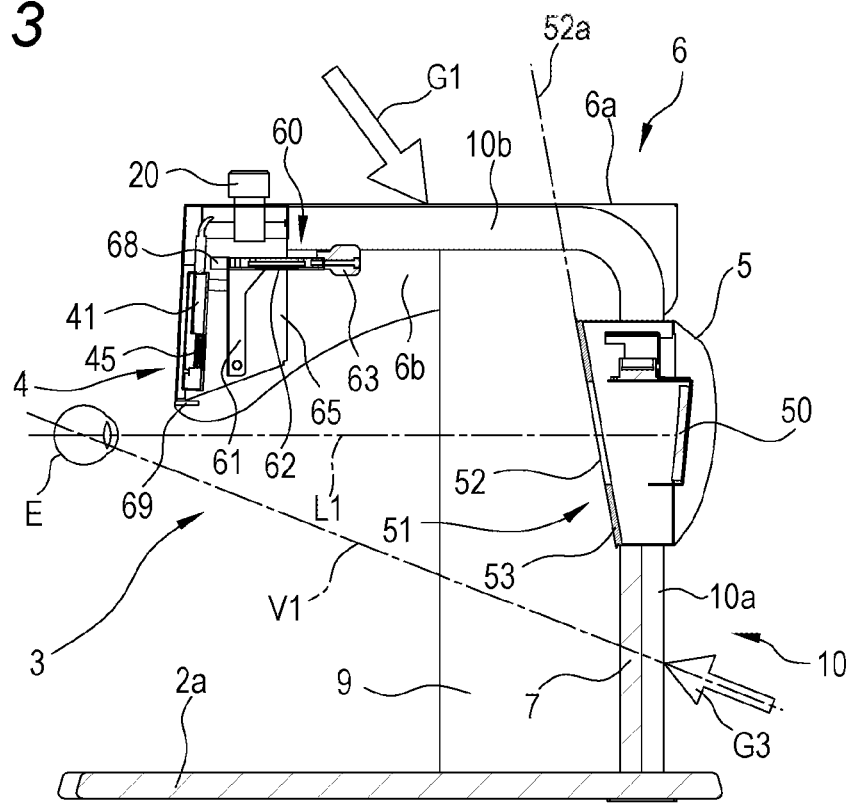
FIG. 3 is a cross sectional view of the optometry apparatus.

In the following, an embodiment of the present disclosure will be described with reference to the drawings. FIG. 1 is an exterior view of the optometry apparatus 1. FIG. 2 is a frontal view of the optometry apparatus 1 as viewed from a direction X in FIG. 1. In the optometry apparatus illustrated in FIG. 2, the subjective eye refractive power measurement unit 8 is placed at the withdrawn position (as will be described in detail below). FIG. 3 is a cross sectional view of the optometry apparatus 1 in an A-A plane of FIG. 2. In FIG. 3, the measurement unit 8 is omitted.

The optometry apparatus 1 is provided with the optometry table unit 2, the target presentation unit 3, and the subjective eye refractive power measurement unit 8 (hereafter simply referred to as "the measurement unit 8"). The optometry table unit 2 is provided with a table 2*a*, an up-down drive unit 2*b* for moving the table 2*a* up or down, and a height adjustment switch 2*c*. The height adjustment switch 2*c* is configured to enable the examiner to input an instruction signal for controlling the up-down movement of the table 2*a*. The up-down drive unit 2*b* is provided with a drive source, such as a motor. The drive source is driven in accordance with the instruction signal input via the switch 2*c*.

The target presentation unit 3 is provided with a target display portion 4, the housing 5, the exterior cover (shield cover) 6, and the optical path switching unit 60. The target display portion 4 includes the display 45 for displaying the target. The housing 5 accommodates the concave mirror 50. The optical path switching unit 60 will be described below.

The target presentation unit 3 is held by the holding unit 10. The holding unit 10 includes the support column 10*a* vertically mounted on the table 2*a*. In a preformed example of the holding unit 10, the housing 5 is attached to the first holding member (support column) 10*a* vertically mounted at the end of the table 2*a*. Namely, the housing 5 is held, by the support column 10*a*. The holding unit 10 includes the second holding member (upper support column) 10*b*. The upper support column 10*b* extends from the support column 10*a*. The upper support column 10*b* extends from the top of the housing 5 toward the examinee (forwardly of the housing 5) so as to hold the display 45. The target display portion 4 is attached to the front portion of the upper support column 10*b*.

The measurement unit 8 is held by the holding unit 10 movably between the measurement position and the withdrawn position. In a preferred example, the measurement unit 8 is supported by the upper support column 10*b* via the support member (such as the support arm) 20 movably between the measurement position and the withdrawn position. In the optometry apparatus 1, the target presentation unit 3, the optometry table unit 2, and the measurement unit 8 may be integrally formed. The optometry apparatus 1 may not be provided with the measurement unit 8.

The measurement unit 8 is provided with a pair of left and right lens chamber units 80. The lens chamber units 80 each include the examination windows 81. In the examination windows 81, various optical elements (such as a spherical lens, a cylindrical lens, and an auxiliary lens) for providing the examinee's eye with a refractive power are disposed in a switchable manner. The measurement unit 8 is provided with the forehead rest 82. The forehead rest 82 sets a predetermined position relationship between the position of the examination windows 81 and the position of the examinees eye. As illustrated in FIG. 1, the examination windows 81 are set to be positioned at the height of the predetermined reference axis L1 at which the target is presented by the concave mirror 50 when the measurement unit 8 is positioned at the measurement position.

At the time of distance-examination, the target presentation unit 3, the target light flux from the display 45 disposed outside the housing 5 is reflected by the concave mirror 50 toward the examinee's eye. The target presentation unit 3 presents the target at an optically predetermined distance-examination distance (such as the examination distance of 5 m). At the time of near-examination, in the target presentation unit 3, the reflective mirror 62 is inserted between the concave mirror 50 and the examinee's eye. Thus, the target light flux from the display 45 is reflected by the reflective member 62 toward the examinee's eye. The target presentation unit 3 presents the target at a predetermined near-examination distance (such as 40 cm). Namely, the target presentation unit 3 is switched to the near optotype presentation unit. The target presentation unit 3 is configured to present the target without going through a beam splitter that would produce a large amount of optical loss in the target light flux. Thus, in the target presentation unit 3, luminance required during examination, such as visual acuity examination, can be ensured without using a display that can emit a large amount of light. Accordingly, the examination can be accurately performed. Further, the housing 5 does not include the beam splitter, so that the housing 5 can be made thin. Thus, the optometry apparatus 1 can provide a space-saving optometry apparatus.

Target Display Portion

As illustrated in FIG. 3, the target display portion 4 is provided with the support portion 41, and the display 45 for displaying the target. The display 45 is supported by the support portion 41. The support portion 41 is held onto a base 65 via a shaft (rotating shaft) 42 which will be described below. The base 65 is supported by the holding unit 10. Thus, the target display portion 4 is supported by the holding unit 10. The display 45 displays the examination target, such as a Landolt ring target. As the display 45, a liquid crystal display (LCD), or an organic electro luminescence (EL) display is used, for example. According to the present embodiment, an LCD is used as the display 45.

Figure 4:
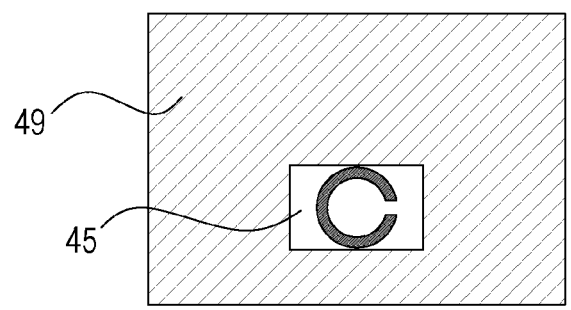
FIG. 4 is a frontal view of a target display portion.

FIG. 4 is a frontal view of the target display portion 4. The display 45 is supported by the support portion 41. On the support portion 41, a substrate and the like of the display 45 which is not illustrated is disposed. On the surface a the support portion 41, a mask plate (cover) 49 is disposed to cover members such as the substrate. The mask plate 49 is disposed around the screen of the display 45. The mask plate 49 prevents a superfluous object around the display 45 from becoming visible to the examinee's eye (examinee). The mask plate 49 is formed from black acrylic resin or of an iron plate painted in black, for example. In this way, the substrate and the like around the display 45 can be suppressed or prevented from being reflected on or around the screen for presenting the target to the examinee's eye. By using the black mask plate 49, the background of the projected target can be made black, whereby the target can be made more recognizable. Obviously, the mask plate 49 may not be black.

Figure 5:
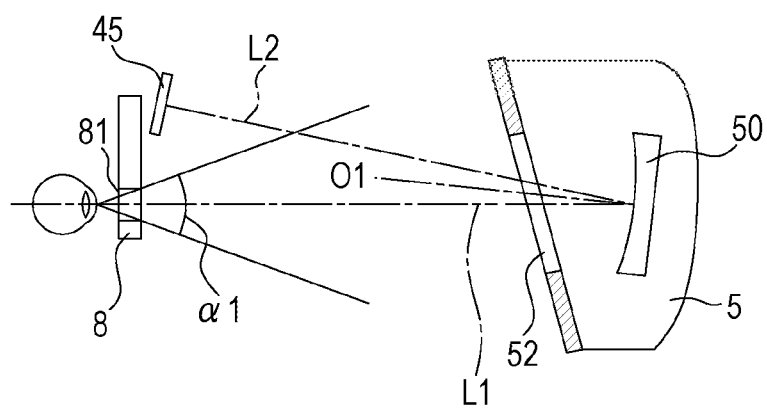
FIG. 5 is at diagram explaining a display disposed position.

FIG. 5 is a diagram explaining a disposed position of the display 45. The display 45 is disposed outside the range of a predetermined visual field angle α1 when the examinee observes the target through the examination window (eye examination window) 81 of the measurement unit 8. Namely, the visual field angle α1 is a visual field angle centered at the reference axis L1 along the direction of the visual line when the examinee's eye (examinee) sees the front through the examination windows 81 of the measurement unit 8. The visual field angle α1 is designed in accordance with the size of the opening of the examination windows 81 on the side of the measurement unit 8 which is farther from the examinee's eye. The visual field angle α1 of the measurement unit 8 is set to 40° with respect to the reference axis L1 at the center, for example. The up-down position of the reference axis L1 substantially corresponds to the measurement optical axis of the examination windows 81 of the measurement unit 8 (the optical axis of the spherical lenses disposed in the examination windows 81). The left-right position of the reference axis L1 substantially corresponds to the left-right central position of the left-right examination windows 81. The concave mirror 50 is disposed on the reference axis L1 along the direction of the visual line (frontal direction) of the examinee's eye placed at the predetermined position.

The concave mirror 50 reflects the target light flux from the display 45 disposed outside the reference axis L1 toward the examinee's eye. Thus, the concave mirror 50 is disposed with the optical axis O1 of the concave mirror 50 (the direction normal to the curved surface of the concave mirror 50) inclined with respect to the reference axis L1. And the display 45 is disposed on an axis L2 which is a reflection axis of the reference axis L1 in the concave mirror 50. The angle of inclination of the screen of the display 45 with respect to the reference axis L1 is set such that an axis perpendicular to the screen of the display 45 (normal direction) is in the direction of the axis L2. Thus, the examinee, when seeing the target from the screen of the display 45 reflected by the concave mirror 50, can see the target on a screen positioned perpendicular to the reference axis L1.

According to the present embodiment, the up-down position of the display 45 is set at a position outside the range of the visual field angle α1 and as close to the reference axis L1 as possible. For example, the display 45 is disposed above the examination windows 81 and near the forehead rest 82 of the measurement unit 8 (namely, the examinee's forehead). The display 45 outputs the target light flux from the examinee's eye side toward the concave mirror 50. The disposed position of the display 45 in the left-right direction is at the center of the examinee directly facing the concave mirror 50.

According to the present embodiment, the inclination angle of the optical axis O1 of the concave mirror 50 with respect to the reference axis L1 is 5°. Namely, the target light flux output from the display 45 is reflected by the concave mirror 50 and guided to the examinee's eye, where the reflection angle is 5°. The inclination angle of the axis L2 of the display 45 with respect to the optical axis O1 is 5°. Namely, the angle of incidence of the target light flux output from the display 45 on the concave mirror 50 is 5°.

The inclination angle of the display 45 and the inclination angle of the concave mirror 50 are set as described above, whereby the development of distortion in the target presented to the examinee's eye can be suppressed. According to the present embodiment the display 45 is disposed near the examinee's forehead, as described above. Thus, when the target light flux is output toward the concave mirror 50, the angle of incidence of the target light flux on the concave mirror 50 and the angle of reflection of the target light flux from the concave mirror 50 are decreased. As a result, distortion in the target can be decreased. Thus, in the optometry apparatus 1, the required space can be reduced and target presentation for accurate examination can be performed while the display 45 is used for displaying the target.

According to the present embodiment, the incident angle is 5° and the reflection angle is 5°. However, these angles are merely examples, and the incident angle and the reflection angle may be set such that distortion is not readily produced in the target.

According to the present embodiment, a small shielding wall 69 is provided under the display 45. Thus, when the optometry apparatus 1 is used in a darkroom or the like, for example, the light flux that directly enters the examinees eye from the display 45 can be efficiently eliminated. According to the present embodiment, the shielding all 69 is a part of the shield cover 6. Namely, the shielding, wall 69 is a portion of the shield cover 6 protruding under the display 45.

By thus disposing the display 45, the examinee's visual field can be extended. When the examinee observes the far optotype within the housing 5 through the target presentation window (transparent panel 52), the examinee does not see the display 45, which is a superfluous structure located closer to the examinee than the protection panel 51. Thus, the examinee is suppressed or prevented from gazing the display 45. As a result, during distance-examination, the development of examinee's eye accommodation due to the examinee seeing a structure other than the target can be decreased. Accordingly, visual function examination can be performed with high accuracy.

According to the present embodiment, the visual field, angle from the examination windows 81 is approximately 40°. However, the visual field angle is not limited to such angle. The optometry apparatus 1 may have different types of measurement units 8. Thus, the examination windows 81 may have various sizes or shapes. Depending on the type, the visual field angle from the examination windows 81 of the measurement unit 8 may vary. The visual field angle may also be varied depending on the distance between the examinees eye and the examination windows 81 of the measurement unit 8. For these reasons, the disposed position of the display 45 may preferably be fine-adjusted in accordance with the visual field angle. Preferably, according to the present embodiment, the examinee's forehead ma be rested on the forehead rest 82. In this way, a certain distance can be maintained between the examinee's eye and the examination windows 81 of the measurement unit 8.

Optical Path Switching Unit

The optical path switching unit 60 is provided with a support portion 61, the reflective mirror (such as the planar mirror) 62, and a knob 63. The optical path switching unit 60 inserts the reflective mirror 62 into or removes it out of the reference axis L1 along, the direction of the visual line of the examinee's eye seeing the front. Thus, the optical path switching unit 60 switches the optical path between the optical path for distance-examination and the optical path for near-examination (as will be described in detail below).

Housing

Figure 6A:
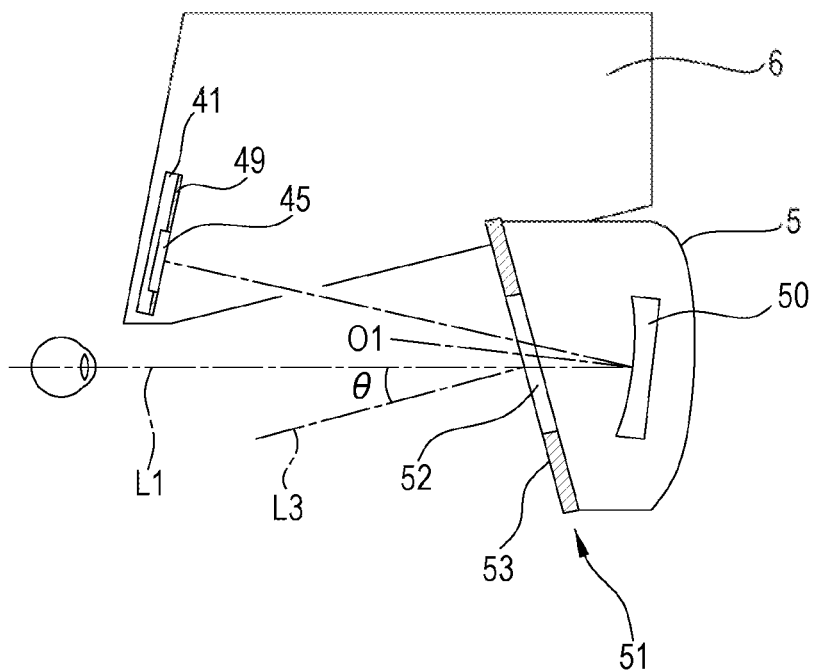
FIGS. 6A and 6B are diagrams illustrating a schematic configuration of a housing.
Figure 6B:
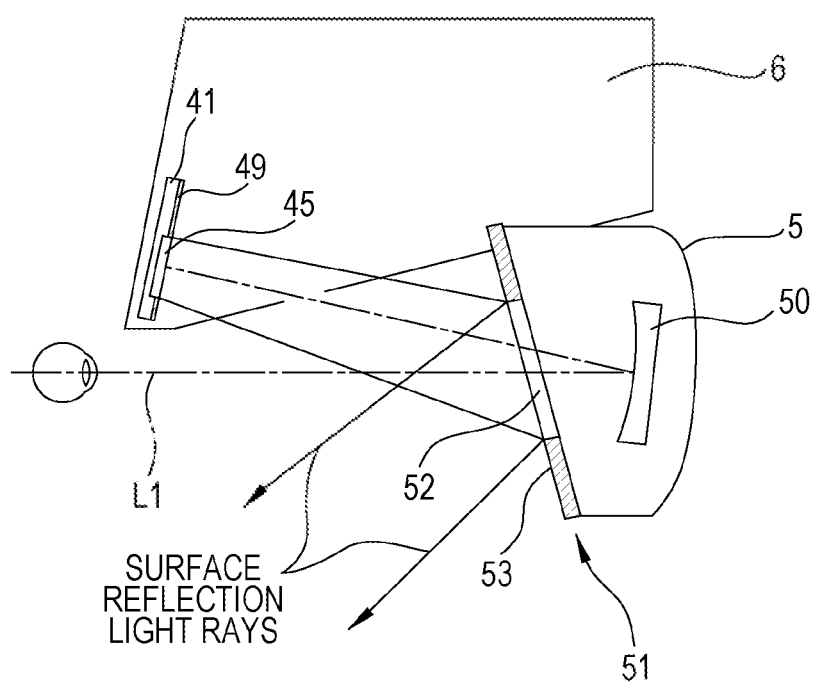

FIGS. 6A and 6B are schematic configuration diagrams of the housing 5. FIG. 6A is a diagram explaining an optical arrangement of various members. FIG. 6B is a diagram explaining surface reflection by the protection panel (protection cover) 51. The housing 5 is a case accommodating the concave mirror 50. The housing 5 includes the protection panel 51 disposed in front of the concave mirror 50 (reflecting surface side). The protection panel 51 is provided with the transparent panel 52 and the shield portion 53. The transparent panel 52 may include a transparent member of acrylic resin or glass plate and the like. The shield portion 53 is disposed around the transparent panel 52. The transparent panel 52 transmits the target light flux from the target display portion 4 (display 45) disposed outside the housing 5. Further, the transparent panel 52 transmits the target light flux reflected by the concave mirror 50 so that the target light flux can be output (obtained) outside the housing 5.

The housing 5 is not limited to a housing case. The housing 5 may be configured to protect the reflecting surface of the concave mirror 50 from dust or external contact. The housing 5 may not have a case-like shape. The housing 5 may not cover a part of the concave mirror 50, or the housing 5 may not cover the rear lace of the concave mirror 50. The concave mirror 50 may be held by the housing 5 at any position around the concave mirror 50. In front of the concave mirror 50, the protection panel is disposed. The holding unit 10 may double as the housing 5.

The transparent panel 52 provides the target presentation window for the examinee to observe the target inside the housing 5. The optometry apparatus 1 presents the examination target to the examinee's eye at a distance of at least 20 cm from the presentation window (transparent panel 52). The examinee sees the target at the center through the transparent panel 52 as the target window. For example, the rear face of the shield portion 53 (inside the housing) is painted in black. The rear face of the shield portion 53 may be affixed with a black filter. The insides of the housing 5 are painted in black, whereby the internal structure is made difficult to see. The housing 5 with the protection panel 51 can suppress or prevent the attachment of dust or scratches to the concave mirror 50, which is formed with high accuracy. The concave mirror 50 is disposed on the reference axis L1 along the direction of the visual line of the examinee's eye seeing the front. The concave mirror 50 is disposed with the optical axis O1 of the concave mirror 50 inclined with respect to the reference axis L1. The focal length of the concave mirror 50 is designed such that the optical distance between the display 45 and the examinees eye is an examination distance of 5 m.

The transparent panel 52 is inclined such that the inclination angle θ of the normal (normal direction) L3 to the plane of the transparent panel 52 with respect to the reference axis L1 is a predetermined angle (such as 10° or more). The inclination angle θ is set at an angle such that, when the light from the target display portion 4 (display 45) is reflected by the surface of the transparent panel 52, the reflected light travels in a direction away ham the examinee's eye. Particularly, the display 45 emits strong light. If the light from the display 45 reflected by the transparent panel 52 enters the examinee's eye, the reflected light interferes With the observation of the target presented via the concave mirror 50. Further, disturbance light from the background rearwardly of the examinee, or disturbance light from above the optometry apparatus 1 may be reflected by the transparent panel 52 and enter the examinee's eye. Such disturbance light also interferes with the target observation by the examinee. In the present apparatus, the inclination angle θ is set as described above, whereby these problems can be mitigated. Further, the required space can be decreased and target presentation for accurate examination can be performed while the display for displaying the target is used.

Upper Shield Member

The upper shield member 6 is provided to block, disturbance light (such as light from a fluorescent light) G1 and G2

(see FIGS. 1 to 3) that would enter the presentation window 52 from above on the examinee (examinee's eye) side of the presentation window 52. Thus, the reflection of disturbance light on the presentation window can be avoided or suppressed. The upper shield member 6 may be configured to suppress the entry of the disturbance light into optical members of the target presentation unit 3 (the display 45, the reflective mirror 62, the protection panel 51, and the concave mirror 50). The upper shield member 6 has a planar structure extending toward the examinee beyond the front face 52a of the presentation window 52 (see FIG. 3), for example. The planar shape of the upper shield member 6 may include a flat shape, a curved shape, or a dome shape.

The upper shield member 6 may include at least one of the first shield member 6a and the second shield member 6b. The first shield member 6a and the second shield member 6b may be formed of the same material or separate materials.

The first shield member 6a may be disposed above the reference axis (specifically, the axis connecting the presentation window 52 and the examinee's eye) L1. The last shield member 6a may be formed in such a manner as to cover the presentation window 32 from diagonally above on the examinee side. The lateral width of the first shield member 6a may be larger than the lateral width of the presentation window 52, or on the same order as the housing 5.

The second shield member 6b may be disposed diagonally above the reference axis L1. The second shield member 6b may be formed in such a manner as to cover the presentation window 52 from diagonally above on the examinee side.

More specifically, the first shield member 6a is disposed over the upper support column 10b, and the second shield member 6b is disposed laterally of the upper support column 10b, for example. The upper shield member 6 covers the top of the optometry apparatus 1 and the sides above the reference axis L1.

Lower Shield Member

A lower shield member 7 is provided to block the examinee's field of view in an area under the presentation window 52. Thus, disturbance light G3 (the light travelling from under the presentation window 52 toward the examinee's eye) that would induce the unwanted examinee's eye accommodation (proximal accommodation) during examination (see FIG. 3) can be blocked. The lower shield member 7 is formed under the presentation window 52, for example. The lower shield member 7 is disposed in such a manner as to cover (block) the visual line V1 of the eye E extending toward the area under the presentation window 52 (see FIG. 3). The lateral width of the lower shield member 7 may be lamer than the lateral width of the presentation window 52, or may be on the same order as the housing 5.

The lower shield member 7 may have a planar structure disposed under the presentation window 52 and substantially perpendicular to the reference axis. The lower shield member 7 may be disposed under the presentation window 52 and configured to block the gap between the presentation window 52 and the table 2a. When the table 2a is absent, the lower shield member 7 may be disposed such that the disturbance light entering the examinee's eye through the area under the presentation window 52 can be decreased.

Lateral Shield Member

The lateral shield members 9 are provided to block the examinee's field of view in areas laterally of the presentation window 52. Thus, disturbance light the light travelling from the sides of the presentation window 52 toward the examinees eye) 04 that would induce the unwanted examinee's eye accommodation (proximal accommodation) during examination can be blocked (see FIGS. 7A and 7B), The lateral shield members 9 are formed laterally of the presentation window 52, for example. The lateral shield members 9 are disposed in such a manner as to cover (block) visual lines V2 of the eyes E extending toward the sides of the presentation window 52 (see FIGS. 7A and 7B), for example. The lateral shield members 9 have planar structures extending from the front face 52a of the presentation window 52 (see FIG. 3) toward the examinee, for example. The lateral shield members 9 may have at planar shape Such as a flat shape, a curved shape, or as dome shape.

The lateral shield members 9 are disposed laterally of the presentation window 52 and to the sides of the reference axis L1, for example. The lateral shield members 9 may have planar structures extending from the left and right sides of the presentation window 52 toward the examinee. The lateral shield members 9 may be configured to shield (or optically block) at least a space extending from the presentation window 52 toward the examinee with a predetermined distance from the sides.

Thus, the lateral shield members 9 block the disturbance light that would enter the examinee's field of view from the sides of the presentation window 52. Namely, the lateral shield members 9 can prevent or suppress the disturbance light that would interfere with eye examination. According to the present embodiment, the lateral shield members 9 extend vertically from the upper support column 10b to the table 2a. However, the configuration of the lateral shield members 9 is not limited to such structure (as will be described in detail below).

When the upper shield member 6, the lower shield member 7, and the lateral shield members 9 are used they may have the same color (such as a dark color) at least in the range of a predetermined visual field angle of the examinee's eye at the optometry position. The predetermined visual field angle may be the visual field angle of the examinee's eye peeking through the examination windows 81. According to the present embodiment, the visual field angle ±20°. However, this is merely an example, and the visual field angle of the examination windows 81 may vary depending on the measurement unit (examination unit) 8. Further, the portions of the upper shield member 6, the lower shield member 7, and the lateral shield members 9 that are in the range of the visual field angle of the examination windows 81 may not be the same color. Preferably, areas around the presentation window 52 may have hale difference in level or inconspicuous boundaries. In this way, the sense of distance created by differences in color or degrees of optical reflection can be made less likely to be induced. The "same color" may include similar colors with little contrast difference and may not be exactly the same color.

When the upper shield member 6, the lower shield member 7, and the lateral shield members 9 are used, the areas of these members that are visible to the examinee's eye E may have the same color as the color of the face of the housing 5 on the examinee side (such as a dark color).

As described above, the optometry apparatus 1 is provided with at least one of the upper shield member 6, the lower shield member 7, and the lateral shield members 9. Thus, the disturbance light that enters the examinee's eye can be limited. Further, the examinee can be less likely to have his visual line guided to the background or shades around the presentation window 52 or reflected light from a surface of the table 2a, or to feel boundaries. Accordingly, causes of proximal eye accommodation can be eliminated. Further, examination accuracy is improved.

According to the present embodiment, the display 45 is disposed outside the housing 5. Thus the chances of the target light flux travelling from the display 45 toward the housing 5 being influenced by disturbance light are high. For this reason, the optical path of the target light flux travelling from the display 45 toward the housing 5 is shielded by the upper shield member 6 from above, whereby the chances of the disturbance light being included in the target light flux can be avoided.

The upper shield member 6, the lower shield member 7, or the lateral shield members 9 may be detachably attached to the optometry apparatus 1. Depending on the environment in which the optometry apparatus 1 is disposed, any of the shield members 6, 7, and 9 may be removed. In this way, the exterior of the optometry apparatus 1 can be simplified.

Figure 11:
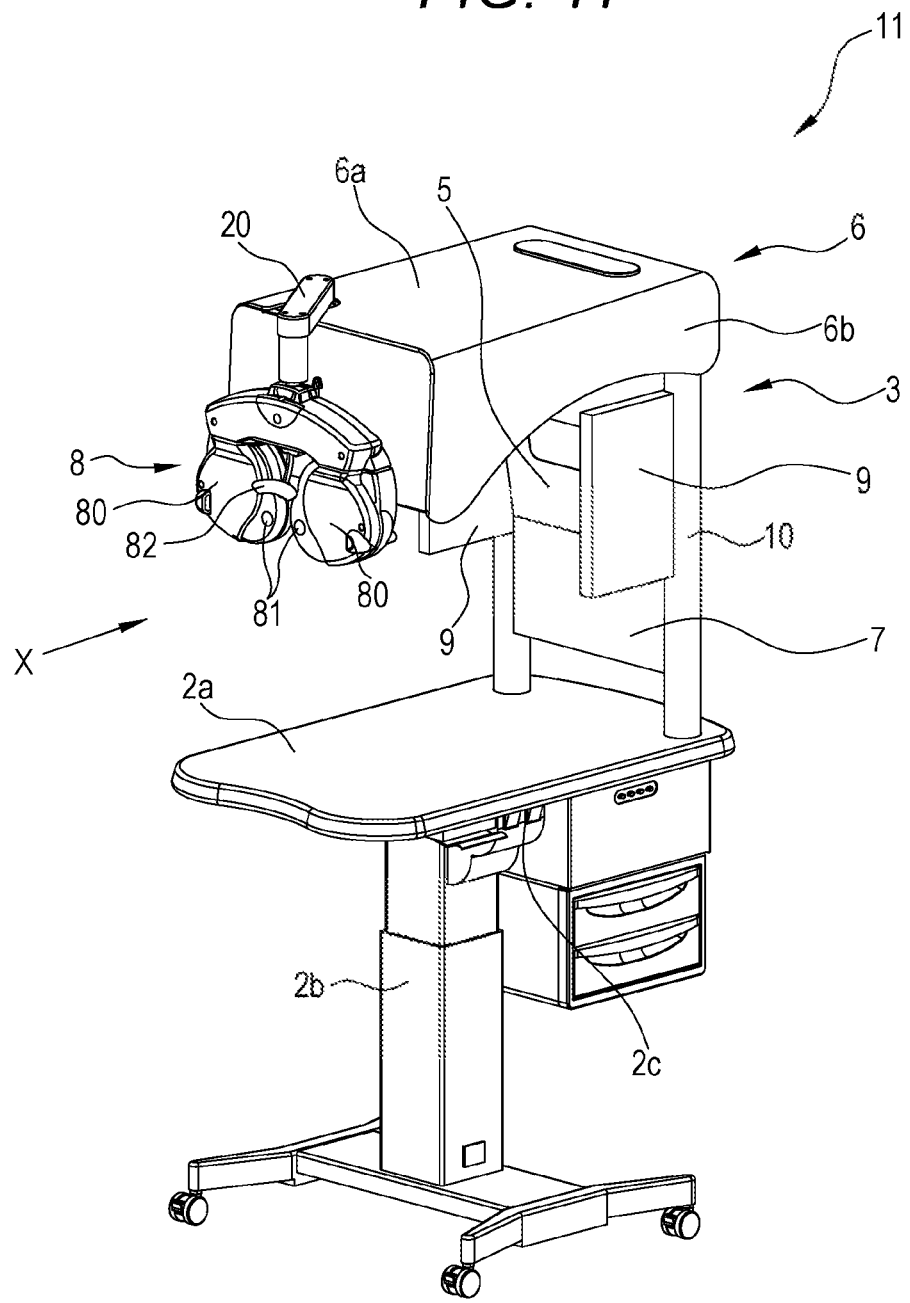
FIG. 11 is a diagram illustrating a modification of the optometry apparatus.

As described above, the lower shield member 7 blocks the gap between the presentation window 52 and the table 2a. The lower shield member 7 may not block the gap between the presentation window 52 and the table 2a completely. As illustrated in FIG. 11, the lower shield member 7 may shield a part of the area under the presentation window 52 so that the disturbance light that would induce the unwanted examinee's eye accommodation during examination can be blocked. The lateral shield members 9 extend vertically from the upper support column 10b to the table 2a. However, the lateral shield members 9 may not block the gap between the upper support column 10b and the table 2a completely. As illustrated in FIG. 11, the lateral shield members 9 may shield the sides of the presentation window 52 so that the disturbance light that would induce the unwanted examinee's eye accommodation during examination can be blocked.

The upper shield member 6, the lower shield member 7, and the lateral shield members 9 according to the present embodiment may have the same color at least in the range of the predetermined visual field angle of the examinee's eye at the optometry position. Further at least a surface of the table 2a near the presentation window 52 that is in the range of the predetermined visual field angle of the examinee's eye at the optometry position may have the same color as the shield members 6, 7, and 9. Thus, the sense of distance created by the difference in color of the shield members 6, 7, and 9 and the table 2a can be made difficult to be induced.

Shield Cover

In order to suppress the entry of disturbance light into the optical members of the target presentation unit 3 (the display 45, the reflective mirror 62, the protection panel 51, and the concave mirror 50), the shield cover 6 is disposed at the upper and side positions of the upper support column 10b of the holding unit 10. The shield cover 6 covers the top of the optometry apparatus 1 and the sides thereof above the reference axis L1. Thus, the entry of disturbance light due to a fluorescent light and the like into the optical members in the apparatus can be suppressed. According to the present embodiment, the shield cover 6 is disposed at the upper and side positions. However this is merely an example, and the shield cover 6 may preferably be disposed at the upper position. The shield cover 6 may not cover the lateral positions.

Mechanism for Moving Subjective Eye Refractive Power Measurement Unit

The support arm 20 mounted on the holding unit 10 supports an upper portion of the measurement unit 8 above the central axis of a face formed by the examination windows 81. Obviously, the portion of the measurement unit 8 that is supported by the support arm 20 is not limited to the upper portion above the central axis of the face formed by the examination windows 81. Any portion of the measurement unit 8 may be supported by the support arm 20.

The support arm 20 is (torsionally) rotatably attached to the holding unit 10. Thus, the measurement unit 8 supported by the support arm 20 is rotatable with respect to the holding unit 10. The examiner places the measurement unit 8 at the examination position in front of the examinee's eye. The examinee rests his forehead on the forehead rest 82 of the measurement unit 8, whereby the examinee's eyes are placed at a certain position. In this state, the examinee observes the target through the examination windows 81 of the measurement unit 8, and visual function examination is implemented.

Figure 7A:
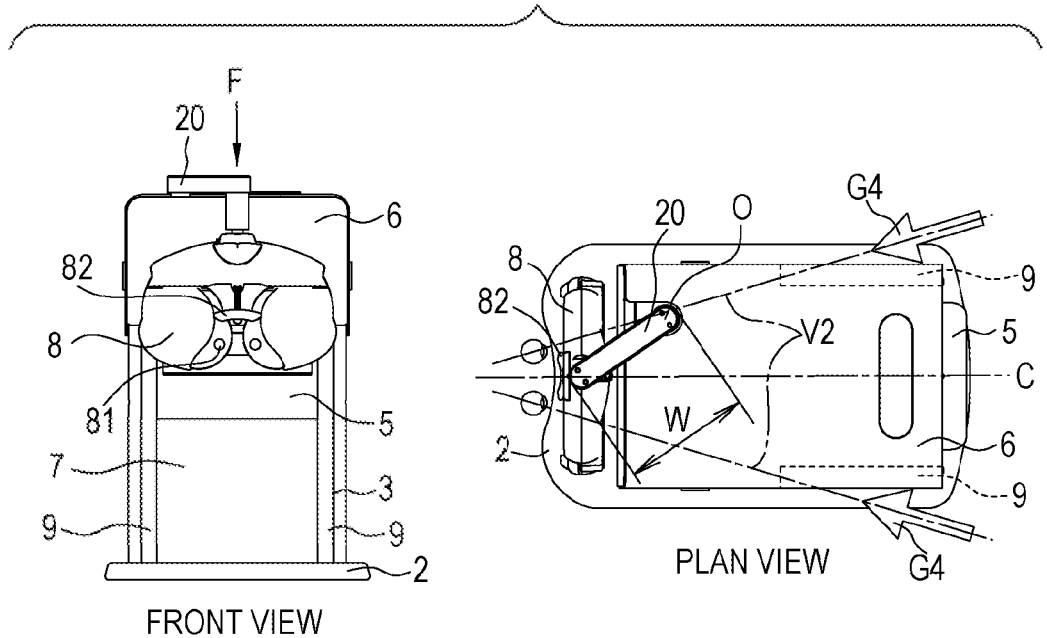
FIGS. 7A and 7B are diagrams explaining the withdrawal of a measurement unit.
Figure 7B:
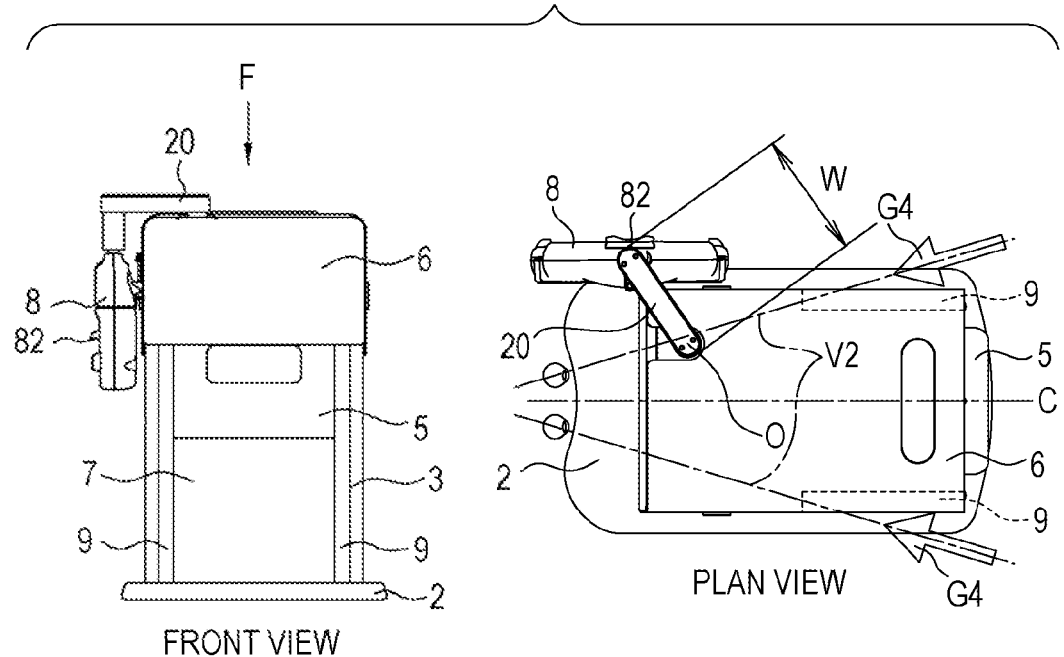

The measurement unit 8 is made rotatable by the support arm 20 with respect to the holding unit 10. FIGS. 7A and 7B are diagrams explaining a withdrawing portion of the measurement unit 8. FIG. 7A shows a frontal view of the apparatus when the measurement unit 8 is placed at the examination position (measurement position), and a plan view of the apparatuses viewed from a direction F. FIG. 7B shows a frontal view of the apparatus when the measurement unit 8 is placed at the withdrawn position, and a plan view of the apparatuses viewed from the direction F.

When the measurement unit 8 is moved between the examination position and the withdrawn position, the measurement unit is rotated along an arc about the connected position O between the support an 20 and the holding unit 10. Namely, the measurement unit 8 is rotated about the connected position O of the support arm 20, whereby the measurement unit 8 is moved between the examination position and the withdrawn position.

When the connected position O is positioned over the central axis C, the distance between the measurement unit 8 and the shield cover 6 or the holding unit 10 is increased so as to prevent interference between the moving measurement unit 8 and the shield cover 6 or the holding unit 10. Namely, the movable range of the measurement unit 8 moving along the arc is increased. As a result, the length W of the support arm 20 is increased.

According to the present embodiment, as illustrated in the plan views of FIGS. 7A and 7B, the connected position O is located at a position displaced from the central axis C of the optometry apparatus 1 in an up-down direction with respect to the sheet of the drawing. When the connected position O is displaced from the central axis C of the optometry apparatus 1 thus, the measurement unit 8 can be moved in a small movable range. Namely, no interference is caused between the measurement unit 8 and the shield cover 6 or the holding unit 10 even when the length of the support arm W is decreased and the movable range of the measurement unit 8 is reduced.

An example in which, as illustrated in the plan views of FIGS. 7A and 7B, the connected position O is positioned above the central axis C to the left with respect to the sheet of the drawing of the frontal view) will be described. In this case, the range of turn (movable range) when the measurement unit 8 is moved to the left of the examinee's eyes is decreased. An example in which the connected position O is positioned below the central axis C to the fight with respect to the sheet of the drawing of the frontal view) in the plan view will be described. In this case, the range of turn (movable range) when the measurement unit 8 is moved to the right of the examinee's eye is decreased.

As described above, the measurement unit 8 is integrally attached to the target presentation unit 3. The connected position O is displaced from the central axis C of the optometry apparatus 1. Thus, the measurement unit 8 can be moved (withdrawn) in at smaller range of movement. This makes it possible to reduce the size of the apparatus and the space required by the apparatus. Further, because the movable range of the measurement unit 8 is decreased, the chances of the measurement unit 8 coming into contact with the examiner are decreased.

According to the present embodiment, the support arm 20 is connected to the upper support column 10*b*. The support arm 20 can be torsionally rotated (turned) about the connected position. The turning of the support arm 20 causes the measurement unit 8 to be moved between the examination position and the withdrawn position. However, this is merely an example, and an up-down moving portion may be attached to the upper support column 10*b* of the holding unit 10 for moving the measurement unit 8 to a withdrawn position higher than the examination position. The measurement unit 8 may be telescopically connected to the holding unit 10 by a known telescopic pipe mechanism. In this case, the measurement unit 8 may be withdrawn by moving the measurement unit 8 in the up-direction (up-down direction). When the up-down moving portion is used, the measurement unit 8 can be prevented from traversing the examiner's face when the measurement unit 8 is moved. Thus, the chances of the measurement unit 8 coming into contact with the examiner can be decreased. Preferably, when the measurement unit 8 is withdrawn by the up-down movement, the measurement unit 8 may not be allowed to enter the visual field of the examinee's eye.

The support arm 20 may include a member configured to move the measurement unit 8 in the up-down direction. Obviously, the withdrawing portion may be configured to move the measurement unit 8 in the up-down direction and turn the measurement unit 8.

Control Portion

Figure 8:
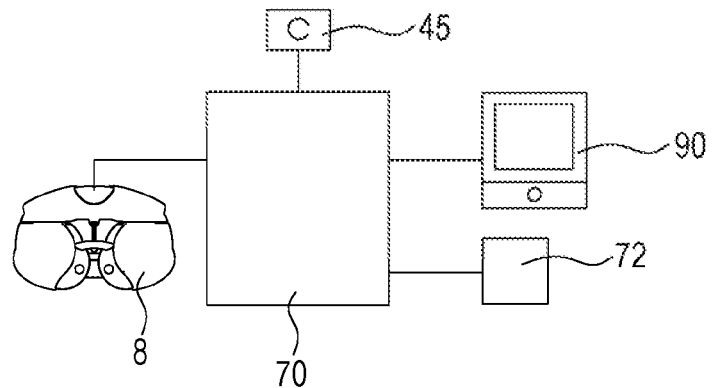
FIG. 8 is a control block diagram of the optometry apparatus.

FIG. 8 is a control block diagram of the optometry apparatus. To the control portion 70, the measurement unit 8 the display 45, a controller 90, a memory 72, and the like are connected. The memory 72 stores a large amount of data about the examination target, such as a Landolt ring target. The memory 72 stores target data corresponding to the eyesight values of 0.1 to 2.0, for example. The control portion 70 calls relevant target data from the memory 72 in response to an input signal from the controller 90. The control portion 70 controls the display 45 to display the called target on the screen of the display 45. According to the present embodiment, the signal from the controller 90 is input to the control portion 70 via a cable which is not shown. The signal from the controller 90 may be input to the control portion 70 by wireless communication using infrared rays, for example.

Optical Path Switching

Figure 9A:
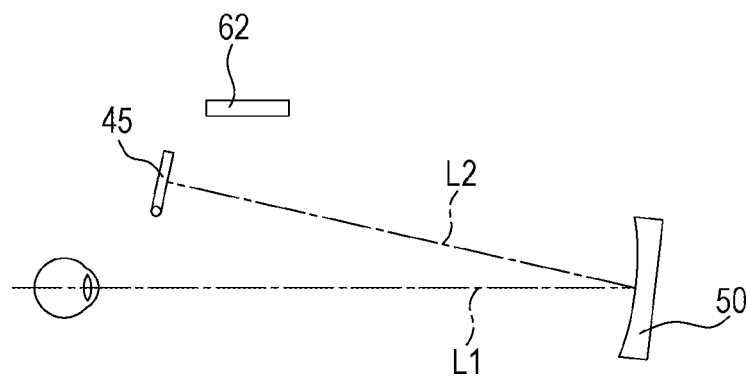
FIGS. 9A and 9B are diagrams explaining the switching between a distance-examination optical path and a near-examination optical path.
Figure 9B:
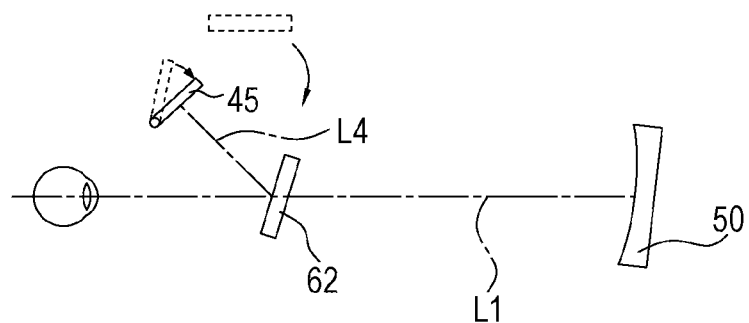

The optometry apparatus 1 is provided with the optical path switching unit 60. The optical path switching unit 60 switches the optical path of the target light flux from the display 45 between the distance-examination optical path and the near-examination optical path. In the following, the optical path switching will be described. FIGS. 9A and 9B are diagrams explaining the switching between the distance-examination optical path and the near-examination optical path. FIG. 9A illustrates the distance-examination optical path. FIG. 9B illustrates the near-examination optical path. In FIGS. 9A and 9B, the measurement unit 8 is omitted.

When the distance-examination optical path is used for visual function examination, the display 45 outputs the target light flux toward the concave mirror 50. The target light flux reflected by the concave mirror 50 is presented to the examinee's eye. The examinee observes the presented target. In this way, distance-visual function examination is implemented.

When the near-examination optical path is used for visual function examination, the reflective mirror 62 is placed on the reference axis L1 between the examinee's eye and the concave mirror 50. Further, the inclination angle of the screen of the display 45 is changed (set) such that the direction normal to the screen of the display 45 is substantially aligned with the direction of the light travelling from the examinee's eye along the reference axis L1 and reflected by the reflective mirror 62 (the direction in which an axis L4 extends).

The target light flux output from the display 45 is guided along the reference axis L1 to the examinee's eye without passing through the concave mirror 50. Because the target light flux is guided to the examinee's eye without passing through the concave mirror 50, the examination distance is decreased (such as 40 cm).

When switching to the distance-examination optical path, the inclination angle of the screen of the display 45 is changed (set) such that the direction normal to the screen of the display 45 is substantially aligned with the direction of the light travelling from the examinee's eye along the reference axis L1 and reflected by the concave mirror 50 (the direction in which the axis L2 extends).

Figure 10A:
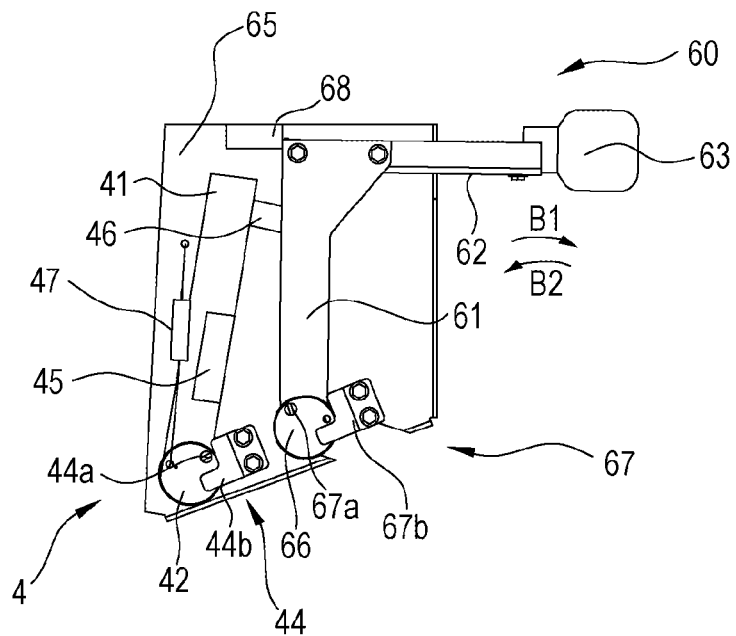
FIGS. 10A and 10B are schematic configuration diagrams of a target display portion and an optical path switching unit portion.
Figure 10B:
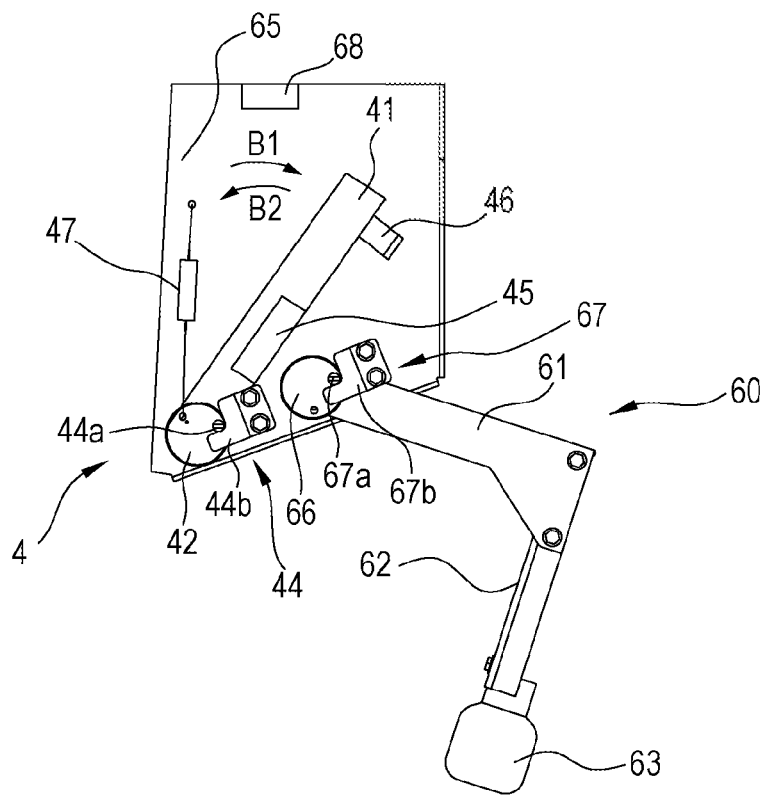

In the following, a configuration for optical path switching will be described. FIG. 10A is a schematic configuration diagram of a portion of the optometry apparatus 1 including the target display portion 4 and the optical path switching unit 60 at the time of the distance-examination optical path. FIG. 10B is a schematic configuration diagram of the portion at the time of the near-examination optical path.

The target display portion 4 is provided with a shaft 42, a rotation limiting portion (a protruding portion 44*a* and a stopper 44*b*) 44, the display 45, as protruding portion 46, and a spring 47 as members for changing the inclination angle of the display 45. The members of the target display portion 4 are held by the base 65. The display 45 is connected to the shaft 42 via the support portion 41. The shaft 42 is held by the base 65 in such a manner that the shaft 42 can be rotated about its own axis. Thus, the inclination angle of the display 45 with respect to the holding unit 10 can be changed.

The spring 47 is connected to the shaft 42. The shaft 42 receives upward force due to the spring force of the spring 47. The spring force causes the shaft 42 to be rotated in a direction B1 (see FIGS. 9A and 9B) at all times (causing the display 45 to be inclined). The amount of rotation is limited by the rotation limiting portion 44. Namely, the inclination angle of the display 45 is limited by the rotation limiting portion 44 to within a predetermined angular range. The rotation limiting portion 44 includes the protruding portion 44*a* and the stopper 44*b*. The protruding portion 44*a* is disposed on the shaft 42. The stopper 44*b* is held by the base 65. When the shaft 42 is rotated by a predetermined amount, the protruding portion 44*a* disposed on the shaft 42 is engaged with the stopper 44*b*, whereby the rotation of the shall 42 is stopped. Thus, the angle of the display 45 is changed (set) to a predetermined inclination angle (LCD inclination angle for near-examination) (see FIGS. 10A and 10B). At the time of distance-examination, the protruding portion 46 disposed on the support portion 41 of the display 45 is pressed in the direction B2 by the support portion 61 of the reflective mirror 62. As a result, the change in the inclination angle of the display 45 is suppressed (see FIG. 10A).

The optical path switching unit 60 is provided with the support portion 61, the reflective mirror (such as the planar mirror) 62, the knob 63, a shaft (rotating shaft) 66, a rotation limiting portion (a protruding portion 67a and a stopper 67b) 67, and a magnet 68. The members of the optical path switching unit 60 are supported by the holding unit 10 via the base 65, similarly to the target display portion 4.

The reflective mirror 62 is connected to the shaft 66 via the support portion 61. The shaft 66 is held by the base 65 in such a manner that the shaft 66 can be rotated about its own axis. Thus, the inclination angle of the support portion 61 with respect to the holding unit 10 can be changed, enabling the reflective mirror 62 to be inserted into or removed out of the optical path (reference axis L1). At this time, the amount of change in the inclination angle is limited by the rotation limiting portion 67 (the protruding portion 67a and the stopper 67b), similarly to the target display portion 4. Namely, the inserted position of the reflective mirror 62 is set by the rotation hunting portion 67.

Further, to the reflective mirror 62, the knob 63 is connected. The examiner operates the knob 63 to insert or remove the reflective mirror 62. At the time of distance-examination, the reflective mirror 62 is held at a position withdrawn from the optical path of the target display portion 4 (withdrawn position) by the magnetic force of the magnet 68 (see FIG. 10A). The magnetic force of the magnet 68 is greater than the spring force of the spring 47 for changing the inclination angle of the display 45 of the target display portion 4. Thus, the magnet 68 presses the support portion 41 via the protruding portion 46 while holding the reflective mirror 62 at the withdrawn position. In this way, the magnet 68 holds the inclination angle of the display 45 at the inclination angle (disposed position) for distance-examination. When the knob 63 is operated by the examiner and the reflective mirror 62 is inserted in the optical path, the magnetic force of the magnet 68 does not act on the protruding portion 46 anymore. As a result, the inclination angle of the display 45 with respect to the reference axis L1 is changed by the spring force of the spring 47 (see FIG. 10B). The inclination angle of the display 45 is set to an angle such that, when the screen of the display 45 reflected on the reflective mirror 62 is seen by the examinee's eye from the direction of the reference axis L1, the screen (virtual screen) is seen as a screen perpendicular to the reference axis L1. When the optical path is switched from the near-examination optical path to the distance-examination optical path, the examiner raises the knob 63, whereby the reflective mirror 62 is moved to the withdrawn position.

According to the present embodiment, the reflective mirror 62 is held in the withdrawn position by the magnet 68. However, this is merely an example, and the optical path switching unit 60 may be provided with a member configured to hold the reflective mirror 62 in the withdrawn position. The member may include a latch.

As described above, the optical path can be easily switched between the optical path for distance-examination and the optical path for near-examination. When the optical path is switched, the inclination angle of the display 45 is changed. Thus, even when the optical path is switched, a distortion-decreased target can be projected onto the examinee's eye. Accordingly, a target for accurate examination can be presented while the display is used for displaying the target.

An examination by target presentation will be briefly described. The examiner instructs the examinee to rest the examinee's forehead onto the forehead rest 82 of the measurement unit 8. When the forehead rest 82 and the forehead are aligned, the examinee's eyes are positioned at a certain position. At the time of distance-examination, the reflective mirror 62 is removed out of the reference axis L1. The target is presented via concave mirror 50 on the reference axis L1 along the direction of the visual line of the examinee's eye seeing the front. The examinee observes the target presented through the examination windows 81 of the measurement unit 8. In this way, visual function examination is performed. The control portion 70 controls the display 45 based on a far optotype selection signal input via the controller 90 to cause the far optotype to be displayed on the display 45. Disturbance light is blocked by the upper shield member 6, the lower shield member 7, and the lateral shield members 9. Thus, the examinee hardly has his visual line guided by the background, shades, or superfluous light, or feels boundaries and experiences proximal eye accommodation. As a result, the examination can be performed with high accuracy.

During near-examination, the reflective mirror 62 is inserted in the reference axis L1 as described above. Further, the angle of the display 45 is changed. The control portion 70 causes the near optotype to be displayed on the display 45 by controlling the display 45 based on the near optotype selection signal input via the controller 90.

Modification

Figure 12:
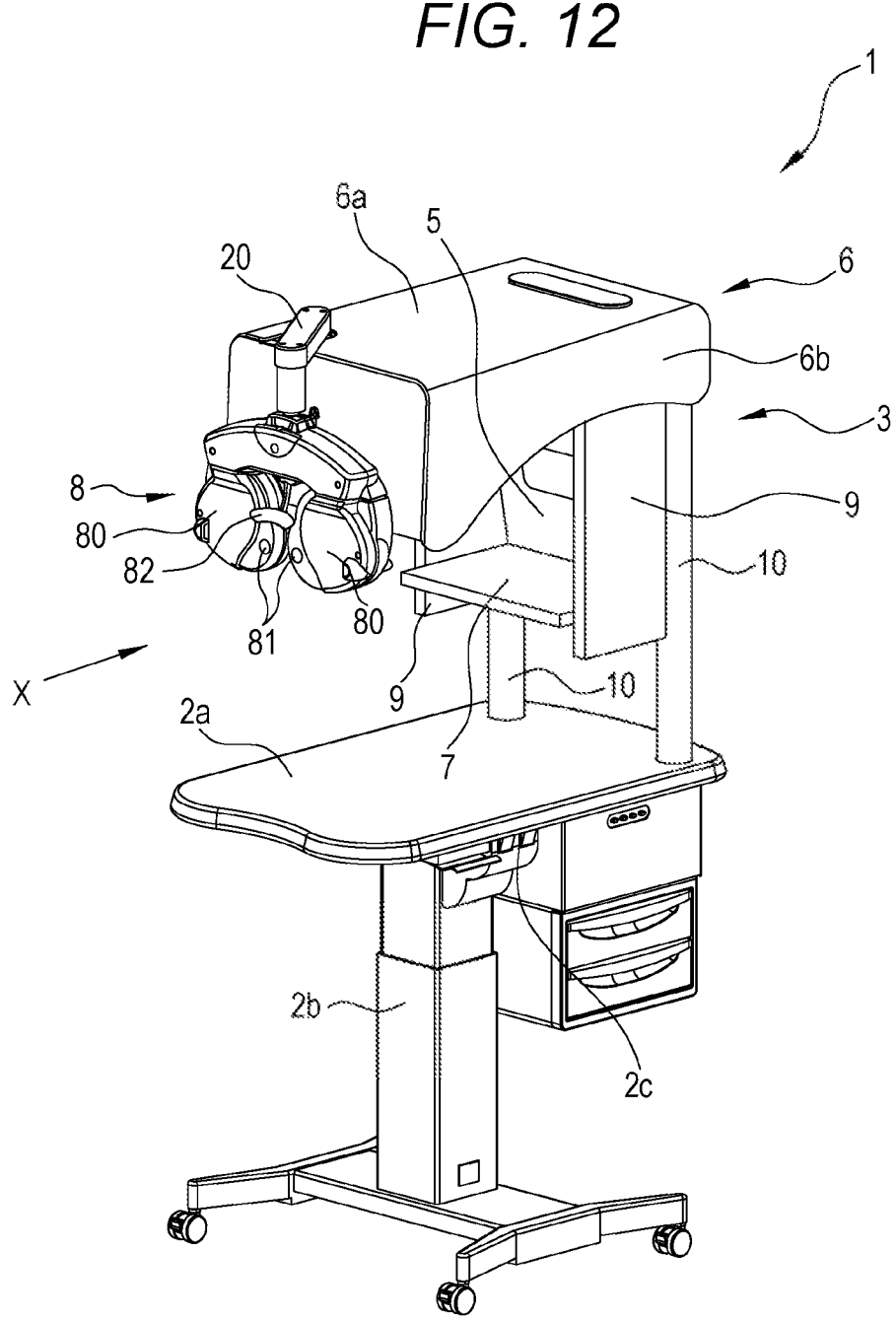
FIG. 12 is a diagram illustrating a modification of the optometry apparatus.

A modification of the embodiment will be described with reference to the drawings. FIG. 12 is a schematic configuration diagram of the present modification. According to the present modification, the lower shield portion 7 extends from under the presentation window 52 toward the examinee. In this respect, the present modification differs from the embodiment described above. The lower shield member 7 shields at least a space extending from the presentation window 52 to the examinee with a predetermined distance.

This configuration also provides effects similar to the effects by the foregoing embodiment. Namely, the lower shield portion 7 blocks disturbance light that would enter the examinee's eye is the gap under the presentation window 52 during examination. Thus, the unwanted examinee's eye accommodation (proximal accommodation) can be eliminated or decreased.

The concave mirror 50 may be placed on the reference axis L1 in the frontal direction when the examinee's eye is seeing the from.

The mask plate 49 is formed of black acrylic resin or an iron plate and the like coated with black paint. In this way, the substrate and the like around the display 45 can be prevented from being reflected in addition to the screen of the target presented to the examinee's eye. The display 45 may be placed outside the range of the predetermined visual field angle α1 from the examination windows 81 when the examinee observes the target by peeking through the examination windows 81 or the measurement unit 8.

The display 45 may be placed on the axis L2 which is a reflection axis of the reference axis L1 in the concave mirror 50. The inclination angle of the screen of the display 45 with respect to the reference axis L1 may be set such that the axis perpendicular to the screen of the display 45 (normal direction) is in the direction of the axis L2. Thus, when the examinee's eye sees the screen of the display 45 reflected by the concave mirror 50, the examinee's eye can see the screen as a screen positioned perpendicular to the reference axis L1.

The angle of incidence on the concave mirror 50 and the angle of reflection from the concave mirror 50 when the target light flux is output toward the concave mirror 50 may be decreased by placing the display 45 near the examinee's forehead. According to the present embodiment, when the examinee observes the far optotype within the housing 5 via the target presentation window (transparent panel 52), the examinee does not see the display 45, which is a superfluous structure closer to the examinee than the protection panel 51. Thus, the examinee can be prevented from gazing the display 45, whereby the intervention of the examinee's eye accommodation caused by seeing structures other than the target during distance-examination can be mitigated.

By placing the display 45 as illustrated in FIG. 3, a wide visual field can be ensured for the examinee. Further, when the examinee observes the far optotype within the housing 5 via the target presentation window (transparent panel 52), the examinee hardly sees the display 45, which is a superfluous structure closer to the examinee than the protection panel 51. Thus, the gazing of the display 45 by the examinee can be substantially eliminated. As a result, the intervention of the examinee's eye accommodation caused by seeing structures other than the target during distance-examination can be mitigated, and the visual function examination can be performed with high accuracy.

The first shield member 6a and the second shield member 6b may be formed of the same member or by separate members.

The measurement unit 8 may be supported on the holding unit 10 by the support arm 20 above the central axis C of a face formed by the examination windows 81 of the measurement unit 8. When the measurement unit 8 is moved between the examination position and the withdrawn position, the measurement unit 8 may be turned along an arc about the connected position O between the support arm 20 and the holding unit 10. Namely, the measurement unit 8 may be moved between the examination position and the withdrawn position with respect to the reference axis L1 (concave mirror 50) by turning the measurement unit 8 about the connected position O of the support arm. The measurement unit 8 may be moved up or down by a configuration with which the support arm 20 is provided for moving the measurement unit 8 up or down. Obviously, the withdrawing portion may be configured to execute up-down movement and rotational movement in combination.

When visual function examination is performed with the near-examination optical path, the reflective mirror 62 may be placed on the reference axis L1 between the examinee's eye and the concave mirror 50. The inclination angle of the screen of the display 45 may be changed such that the direction normal to the screen of the display 45 is substantially aligned with the direction of the axis L4 produced by reflection of the reference axis L1 by the reflective mirror 62.

The optometry apparatus according to an embodiment the present disclosure may be any of the following first to fifth optometry apparatuses.

The first optometry apparatus includes a housing with a presentation window for presenting an examination target in a frame, the optometry apparatus presenting the target to an examinee's eye at a distance of at least 20 cm from the presentation window and including: an upper shield member for blocking disturbance light entering the presentation window from above the examinee's eye; and a lower shield member for shielding an area under the presentation window so as to block the examinee's field of view in the area under the presentation window.

The second optometry apparatus is according to the first optometry apparatus, wherein the upper shield member and the lower shield member have the same color at least in the range of a predetermined visual field angle of the examinee's eye at an optometry position.

The third optometry apparatus is according to one of the first and the second optometry apparatuses, further including a lateral shield member extending from each of left and right sides of the presentation window toward the examinee, and blocking at least a space where the examinee's eye turns from the presentation window toward the examinee with a predetermined distance, the lateral shield member having the same color as the upper shield member and the lower shield member in at least the range of the predetermined visual field angle of the examinee's eye at the optometry position.

The fourth optometry apparatus is according to any one of the first to the third optometry apparatuses, wherein the lower shield member extends from under the presentation window toward the examinee, and shields at least a space where the examinee's eye turns film the presentation window toward the examinee with a predetermined distance.

The fifth optometry apparatus is according to any one of the first to the fourth optometry apparatuses, further including: a concave mirror disposed in the housing; and a target projection portion disposed outside the housing for projecting a target light flux onto the concave mirror, wherein the target light flux is projected onto the examinee's eye via the concave mirror, and the upper shield member shields an optical path of the target light flux from above.

According to the first to the fifth optometry apparatuses, target presentation for accurate examination can be performed. Further, the influence of disturbance light can be decreased.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described, above are disclosed as example forms of implementing the claims appended hereto.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An optometry apparatus comprising:
   a housing accommodating a concave mirror disposed on a reference axis;
   a display disposed outside the housing and out of the reference axis for projecting a target light flux onto the concave mirror; and
   a transparent panel disposed on an outer surface of the housing on the reference axis, and configured to transmit the target light flux from the display, re-transmit the target light flux reflected by the concave mirror, and output the target light flux from the housing, wherein the concave mirror is configured to reflect the target light flux output from the display toward an examinee's eye along the reference axis, a whole of the display is disposed in the direction of the reference axis between the examinee's eye and an edge of the concave mirror, the edge being a closest portion of the concave mirror to the examinee's eye, the transparent panel is disposed such that a direction from the transparent panel to the examinee's eye and normal to the transparent panel is inclined downward with respect to the reference axis, and the concave mirror is disposed such that a direction of an optical axis of the concave mirror from the concave mirror to the examinee's eye is inclined upward with respect to the reference axis.

2. The optometry apparatus according to claim 1, comprising:
   the housing having a presentation window for presenting an examination target in a frame to the examinee's eye at a distance of at least 20 cm;
   an upper shield member for blocking disturbance light entering the presentation window from above the examinee's eye; and
   a lower shield member for shielding an area under the presentation window.

3. The optometry apparatus according to claim 2, wherein the upper shield member and the lower shield member have the same color at least in the range of a predetermined visual field angle of the examinee's eye at an optometry position.

4. The optometry apparatus according to claim 3, further comprising a lateral shield member extending from each of left and right sides of the presentation window toward the examinee, and optically shielding a space extending from the presentation window toward the examinee with a predetermined distance, wherein
   the lateral shield member has the same color as the upper shield member and the lower shield member at least in the range of the predetermined visual field angle of the examinee's eye at the optometry position.

5. The optometry apparatus according to claim 2, wherein the lower shield member extends from under the presentation window toward the examinee, and is configured to optically shield a space extending from the presentation window toward the examinee with a predetermined distance.

6. The optometry apparatus according to claim 1, wherein:
   the housing includes a shield member disposed on a front face side of the concave mirror and around the transparent panel; and
   the transparent panel surrounded by the shield member includes a presentation window for observation of a target within the housing by the examinee's eye.

7. The optometry apparatus according to claim 1, further comprising an eye refractive power measurement unit, wherein:
   the eye refractive power measurement unit includes a pair of left and right lens chamber units;
   the lens chamber units include an examination window and optical elements disposed in the examination window in a switchable manner; and
   the eye refractive power measurement unit is disposed with the examination window positioned at the same height as the reference axis.

8. The optometry apparatus according to claim 7, comprising a target presentation unit including the housing and the display, the target presentation unit including a support portion movably supporting the eye refractive power measurement unit between an examination position in front of the examinee's eye and a withdrawn position.

9. The optometry apparatus according to claim 7, wherein the display is disposed outside the range of a predetermined visual field angle of the examinee's eye peeking through the examination window.

10. The optometry apparatus according to claim 9, wherein:
    the housing includes a presentation window disposed on a front face of the concave mirror, and is disposed in a frontal direction of the eye refractive power measurement unit; and
    the display is disposed at a position such that the target light flux from the display travels from outside the housing toward the concave mirror via the presentation window.

11. The optometry apparatus according to claim 1, wherein:
    the optometry apparatus includes the single display; and
    the concave mirror is disposed at an optically predetermined examination position for distance-examination on the reference axis;
    the optometry apparatus further comprising:
    an optical path switch portion including a reflective member configured to be inserted in or removed from an optical path from the single display to the examinee's eye, the optical path switch portion configured to switch the optical path from the single display to the examinee's eye between an examination optical path for distance-examination and an examination optical path for near-examination by inserting the reflective member in or removing the reflective member out of the optical path, the examination optical path for distance-examination and the examination optical path for near-examination starting from the single display; and
    a first angle changing portion for changing an inclination angle of a screen of the single display in accordance with whether the examination is distance-examination or near-examination.

12. The optometry apparatus according to claim 11, wherein:
    the reflective member is configured to, when inserted in the optical path from the display to the examinee's eye, reflect the target light flux output from the display toward the examinee's eye along the reference axis;
    the optical path switch portion switches the optical path from the display to the examinee's eye to the examination optical path for near-examination by inserting the reflective member at an examination position for near-examination between the concave mirror and the examinee's eye; and
    the optical path switch portion switches the optical path from the display to the examinee's eye to the examination optical path for distance-examination by removing the reflective member from the examination position for near-examination.

13. The optometry apparatus according to claim 12, wherein the first angle changing portion is configured to, when the reflective member is inserted in the examination position for near-examination, change the inclination angle of the screen of the display such that a direction normal to the screen of the display is substantially aligned with the direction of the light travelling from the examinee's eye along the reference axis and reflected by the reflective member.

14. The optometry apparatus according to claim 11, wherein a direction normal to the screen of the display with respect to an optical axis of the concave mirror is inclined such that the target light flux from the display enters the concave mirror with a displacement with respect to the optical axis.

15. The optometry apparatus according to claim 1, wherein the display is disposed above the examinee's eye, and
an angle between an axis normal to the display and an optical axis of the concave mirror is set such that the target light flux projected from the display and reflected by the concave mirror is guided to the examinee's eye.

16. The optometry apparatus according to claim 15, wherein the angle is about 5°.

17. The optometry apparatus according to claim 1, wherein the display is configured to output the target light flux from a side of the examinee's eye toward the concave mirror.

18. The optometry apparatus according to claim 1, wherein the transparent panel is disposed, in a direction of the reference axis, between the display and the concave mirror and between the concave mirror and an examinee's eye.

\* \* \* \* \*